United States Patent [19]

Awh et al.

[11] Patent Number: 5,554,155
[45] Date of Patent: Sep. 10, 1996

[54] FIBER OPTIC PICK MANIPULATOR

[75] Inventors: Carl C. Awh, Lutherville; R. Scott Rader, Baltimore; Alexander C. Walsh, Hunt Valley; Eugene de Juan, Jr., Phoenix, all of Md.

[73] Assignee: Johns Hopkins University, Baltimore, Md.

[21] Appl. No.: 253,917

[22] Filed: Jun. 3, 1994

[51] Int. Cl.$^6$ .............................. A61B 17/36; A61F 9/007
[52] U.S. Cl. .................. 606/16; 606/161; 604/20; 604/289; 604/294; 604/902
[58] Field of Search .................... 128/4, 6, 7, 757, 128/758; 604/22, 46, 47, 55, 264, 289, 294, 902; 606/4–6, 16, 107, 159–162; 600/156, 20; 433/31, 91

[56] References Cited

U.S. PATENT DOCUMENTS

| | | | |
|---|---|---|---|
| 4,245,624 | 1/1981 | Komiya | 128/4 |
| 4,448,188 | 5/1984 | Loeb | 128/6 |
| 4,578,059 | 3/1986 | Fabricant et al. | 604/289 X |
| 4,878,487 | 11/1989 | Sinnett . | |
| 4,992,047 | 2/1991 | Warner | 604/902 X |
| 4,998,527 | 3/1991 | Meyer | 128/6 |
| 5,078,712 | 1/1992 | Easley et al. | 606/16 |
| 5,123,840 | 6/1992 | Nates | 604/902 X |
| 5,154,694 | 10/1992 | Kelman | 604/22 |
| 5,201,730 | 4/1993 | Easley et al. | 606/4 |
| 5,230,621 | 7/1993 | Jacoby | 600/156 |
| 5,346,469 | 9/1994 | Ikeda et al. | 604/22 |

OTHER PUBLICATIONS

McCuen et al; A Fiberoptic Diathermy Tissue Manipulator For Use In Vitreous Surgery; American Journal of Opthalmology; Dec. 1984; p. 803–804.

*Primary Examiner*—Richard J. Apley
*Assistant Examiner*—John P. Leubecker
*Attorney, Agent, or Firm*—Cushman Darby & Cushman, LLP

[57] ABSTRACT

A multi-function pick-manipulator device that provides the functions of a vitreoretinal pick, fiberoptic illumination, and irrigation/aspiration. The manipulator may also function as a bipolar diathermy device. To provide a compact, multi-function device, the aspiration tube projects distally beyond the distal end of the fiber optic containing support tube of the manipulator. The projecting aspiration tube is bent and shaped at its tip to define a pick-like structure that extends in a direction generally transverse to the axis of the fiber optics. An aspiration opening is defined through the wall of the aspiration tube proximal to the pick-like tip.

18 Claims, 1 Drawing Sheet

FIBER OPTIC PICK MANIPULATOR

BACKGROUND OF THE INVENTION

1. Field of the Invention

The present invention relates to a manipulator for intraocular surgery and, more particularly, to a multi-function instrument that may advantageously be used during bimanual vitreoretinal surgery. The pick-manipulator of the invention can provide the functions of a vitreoretinal pick, fiberoptic illumination, bipolar diathermy, and irrigation/aspiration of fluids and tissues in a single 19 or 20 gauge instrument.

2. Description of the Related Art

A fiberoptic tissue manipulator is a device used in intraocular surgery to illuminate and to control objects in the surgical field by means of aspiration or irrigation of fluid. Tissue membranes may be peeled, picked up, or aspirated after cutting. Blood and air bubbles can also be cleared from the field by means of suction or irrigation. Aspiration is achieved via a small tube, usually of stainless steel or Kevlar, which can be inserted into the eye. This is connected to an intermediate tube, typically of silicone, to a terminal device such as a syringe or, in the event more advanced control is desired, an automated aspiration control system (such as the Storz Premiere). Light is provided to the surgical field by an illuminating fiber optic. In many conventional devices the fiber optic lies alongside of the aspiration passage in a larger delivery tube. An exemplary fiberoptic manipulator, detailed by McCuen and Hickingbotham in "A fiberoptic diathermy tissue manipulator for use in vitreous surgery", *Am J Ophthalmol.* 1984; 98; 803–804, also provides bipolar diathermy functions. As is apparent from the foregoing, however, tissue control in known fiberoptic manipulators is limited to aspiration and infusion or irrigation.

During tissue manipulation, it frequently occurs that a pick-like instrument is required to manipulate the tissue, thus requiring that a further instrument be introduced into the surgical field. This requires the manipulation of multiple instruments and/or may require that instruments be temporarily switched. Known pick like instruments, which have no aspiration/infusion capabilities, are exemplified by the fiberoptic pick disclosed in U.S. Pat. No. 4,878,487.

SUMMARY OF THE INVENTION

It is an object of the present invention to provide an improved fiberoptic manipulator which incorporates a pick instrument so that an added picking function can be provided without increasing the complexity of the manipulator and so that the need to switch instruments during the procedure is eliminated.

In accordance with the present invention a manipulator device is provided wherein the distal section of the aspiration tube extends beyond the walls of the larger delivery/fiber optic tube and is bent and curved. The extension thus provides a pick-like instrument for use during the surgical procedure.

Thus, the foregoing and other objects of the invention are realized by providing a manipulator that comprises a generally tubular support member having a proximal end and a distal end and a lumen extending therethrough between the proximal and distal ends. At least one fiber optic fiber extends through the tubular support member and preferably terminates distally substantially coincident with the distal end of the support member. An aspiration passage extends through the tubular support and includes an aspirator tube which extends distally beyond the distal end of the support tube. The aspirator tube has a generally straight portion extending from the distal end of the support tube and a curved portion extending distally from a distal end of the straight portion. The curved portion terminates distally in a pick-like tip. An aspiration lumen is defined at least through the straight portion and terminates distally in an aspiration opening.

Other objects, features, and characteristics of the present invention as well as the methods of operation and functions of the related elements of the structure, and the combination of parts and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION OF THE PRESENTLY PREFERRED EXEMPLARY EMBODIMENTS

Figure 1:
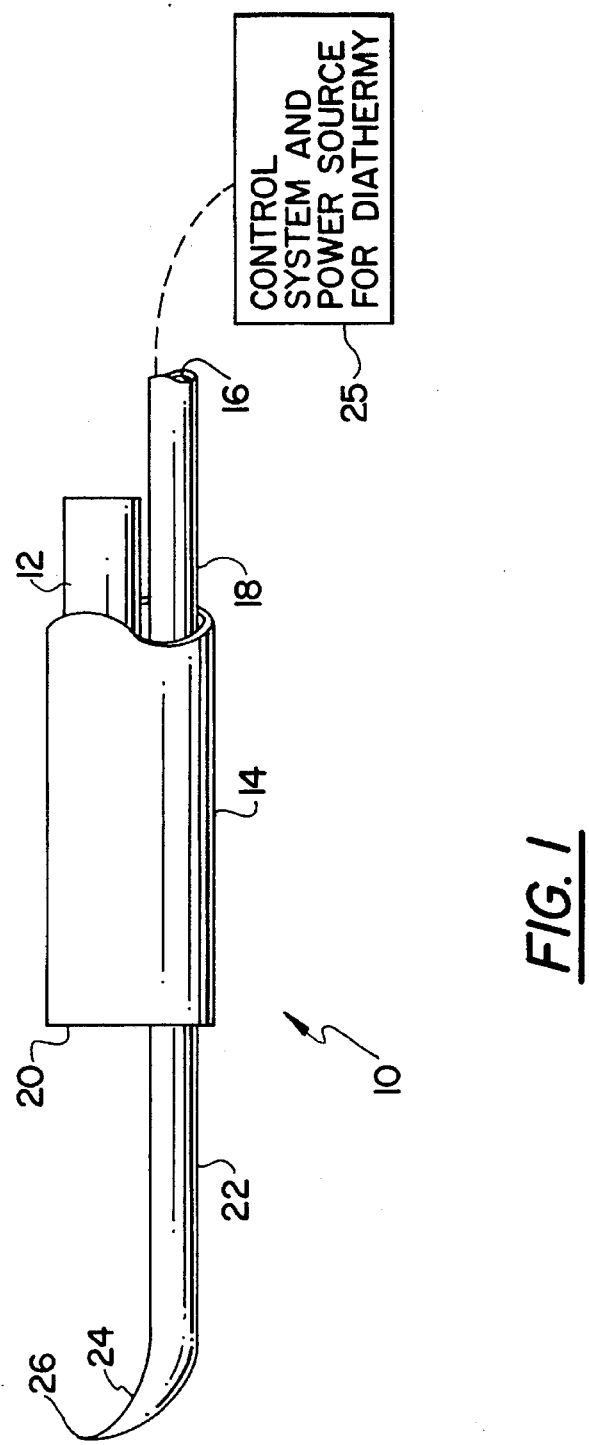
FIG. 1 is a schematic elevational view of a pick manipulator provided in accordance with the invention.

The tip or distal end 10 of a pick manipulator provided in accordance with the present invention is schematically shown in FIG. 1. The manipulator also has a handle or handpiece (not shown) extending proximally from the illustrated distal end 10. The handpiece is operatively coupled to one or more control systems (not shown) in a conventional manner.

To illuminate the surgical field, a fiber optic element or elements 12 are provided to extend longitudinally of the larger delivery or support tube 14. An aspiration passage 16 is also defined within the delivery tube so as to extend substantially parallel to the fiber optics 12. In the illustrated embodiment, the aspiration passage 16 is defined by a tube 18 disposed within the support tube 14. The fiber optics 12 preferably terminate distally at the distal end 20 of the larger delivery or support tube 14. The aspiration tube 18, however, extends beyond the distal end of the support tube 14 and includes a straight portion 22 and a curved portion 24. The distal-most portion of the aspiration tube thus is bent and ground or sanded to a curve and terminates distally in a tapered pick-like tip 26.

In the illustrated embodiment, the aspiration passage 16 terminates distally in an elliptical distal opening 28. That opening is offset with respect to a longitudinal axis of the aspiration passage 16 as defined within the delivery tube. The tip 10 of the manipulator is preferably a thin walled 19 or 20 gauge stainless steel tube 14 that supports and contains the aspiration tube 18 and light fiber(s) 12. Disposed within this tube 14, in the preferred embodiment, is a 0.5 mm (0.020") or 0.762 mm (0.030") plastic or acrylic light fiber or other known fiber optic 12 and a regular wall 30 or 31 gauge stainless steel aspiration tube 18. As noted above, the fiber optic 12 may be a single optical fiber or a bundle of optical fibers, as necessary or desirable.

The pick manipulator of the invention may further provide a bipolar diathermy function. More particularly, by electrically insulating the aspiration tube 18 from the outer tube 14, in a known manner, providing suitable electrical connections at the proximal end of aspiration tube 18, and providing a suitable control system and power source schematically shown at 25, the pick tip 26 can function as a footpedal-controlled coaxial bipolar diathermy device.

Figure 2:
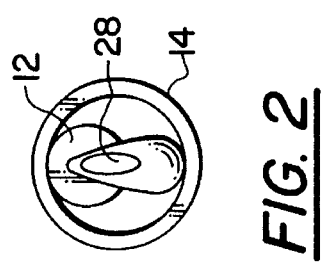
FIG. 2 is an end view of the pick manipulator.

The aspiration tube 18 extends beyond the distal tip of the 19 gauge tube and is bent and ground to an intercepting curve to produce pick 26, as noted above. The intercepting curve of the outer tube wall results in an elliptical hole 28 (FIG. 2) on the bottom of the tube so that things may still be picked up with the instrument. Tube 18 is used for aspiration only as long as necessary in the procedure. Once within the handle (not shown) of the manipulator device, the aspiration tube 18 opens up immediately to, for example, a 21 gauge tube (not shown) which is connected outside the manipulator handle to a silicone tube (not shown). It is important and advantageous to maximize both the fiber diameter and the aspiration capability. For this reason, the small aspiration tube must open up to a larger tube as quickly as possible in order to ease the transmission of fluid and other materials, thereby minimizing the risk of clogging. In addition, the fiber and tube sizes can be optimized by looking at different configurations inside the delivery tube 14. A thin wall or extra thin wall delivery tube should be used because the delivery tube strength is less relevant as a factor than maximizing its internal volume. The configuration detailed above was selected because it provides sufficient light while still providing for good aspiration.

The distal most tip of the aspiration tube may be bent at its tip using standard small tube bending procedures. Great care must be taken not to buckle the walls, not to distort the thin metal at the tip of the pick, and to preserve the surface quality of the metal to minimize corrosion. The light fiber 12 and aspiration tube 18 are glued into the delivery tube 14 making sure that the plane of symmetry of the pick intersects the center line of the fiber and, that the pick extends a desirable distance beyond the end of the delivery tube and beyond the end of the optical fiber.

The pick manipulator of the invention may be used just like any simple manipulator. The pick may be used in addition to aspiration to peel or move objects as necessary or desirable. With the instrument of the invention, infusion is particularly useful during removal of intraocular blood. Gentle infusion can blow pooled blood off of the retinal surface, allowing safe aspiration through a vitreous cutter. When combined with diathermy, infusion allows prompt exposure and coagulation of bleeding sites. Aspiration-manipulation is most effective when epiretinal membranes are under minimal or no traction and can fully occlude the port. Such membranes can be aspirated and appropriately manipulated during tissue dissection. Diathermy can also be used during gentle aspiration of vascularized tissues. The vitreoretinal pick tip is used to elevate or dissect membranes that are not amenable to aspiration. As is apparent from the foregoing, by virtue of its diverse functional attributes, the manipulator of the invention can be used to handle tissue or fluid or any consistency.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A manipulator comprising:

an elongated support member having a proximal end and a distal end;

at least one optical fiber extending through at least a portion of said support member; and an aspiration passage extending through at least a portion of said support member and including an aspiration tube which extends distally beyond said distal end of said support member, said aspiration tube having a generally straight portion extending from said distal end of said support member and a curved portion extending distally from a distal end of said straight portion, said curved portion terminating distally in a pointed pick tip;

an aspiration lumen being defined through at least a portion of said straight portion and terminating distally in an aspiration opening, said pointed pick tip being substantially closed and said aspiration opening being defined at said curved portion, spaced from said pointed pick tip.

2. A manipulator as in claim 1, wherein a center of said aspiration opening is laterally offset from a central axis of said aspiration lumen in said straight portion of said aspiration tube.

3. A manipulator as in claim 1, wherein said aspiration opening is generally elliptical.

4. A manipulator as in claim 1, wherein a plane of symmetry of said pick tip intersects a center line of said optical fiber.

5. A manipulator as in claim 1, wherein said tip is axially spaced a pre-determined distance from said distal end of said support member.

6. A manipulator as in claim 1, wherein said support member is a tube of about 19–20 gauge.

7. A manipulator as in claim 1, wherein said straight portion of said aspiration tube is about 30–31 gauge.

8. A manipulator as in claim 1, wherein said aspiration passage further includes a tubular member substantially continuous with and extending proximally from said aspiration tube.

9. A manipulator as in claim 1, wherein said aspiration tube is formed from a metal material.

10. A manipulator as in claim 1, wherein said support member is formed from a metal material.

11. A manipulator as in claim 1, wherein said optic fiber is formed from a polymeric material.

12. A manipulator as in claim 1, wherein said at least one optical fiber terminates distally substantially coincident with the distal end of the support member.

13. A manipulator as in claim 1, wherein said support member and said aspiration tube each have a generally circular cross-section.

14. A manipulator as in claim 1 wherein said elongated support member is generally tubular having a lumen extending therethrough between said proximal and distal ends, said at least one optical fiber and said aspiration passage each extending through at least a portion of said lumen.

15. A manipulator as in claim 1, further comprising means for providing a diathermy function at least at said pick tip.

16. A manipulator comprising:

an elongated support member having a proximal end and a distal end;

at least one optical fiber extending through at least a portion of said support member; and an aspiration passage extending through at least a portion of said support member and including an aspiration tube which extends distally beyond said distal end of said support member, said aspiration tube having a generally straight portion extending from said distal end of said support member and a curved portion extending distally from a distal end of said straight portion, said curved portion terminating distally in a pointed pick tip;

an aspiration lumen being defined through at least a portion of said straight portion and terminating distally in an aspiration opening, wherein a plane of symmetry of said pointed pick tip intersects a center line of said optical fiber.

17. A manipulator as in claim 16, wherein said pointed pick tip is substantially closed and said aspiration opening being defined in said curved portion, from said pointed pick tip.

18. A manipulator as in claim 16, further comprising means for providing a diathermy function at least at said pick tip.

* * * * *